(12) United States Patent
Riccio (10) Patent No.: US 10,857,399 B2
(45) Date of Patent: Dec. 8, 2020

(54) PATIENT RESPIRATORY MASK WITH INTEGRATED MICROPHONE AND METHOD OF PATIENT COMMUNICATION UTILIZING THE SAME

(71) Applicant: Lucca Ventures, Inc., Southington, CT (US)

(72) Inventor: Lucca Riccio, Southington, CT (US)

(73) Assignee: Lucca Ventures, Inc., Southington, CT (US)

( * ) Notice: Subject to any disclaimer, the term of this patent is extended or adjusted under 35 U.S.C. 154(b) by 645 days.

(21) Appl. No.: 15/611,136

(22) Filed: Jun. 1, 2017

(65) Prior Publication Data

US 2017/0368383 A1 Dec. 28, 2017

Related U.S. Application Data

(60) Provisional application No. 62/353,099, filed on Jun. 22, 2016.

(51) Int. Cl.
| | | |
|---|---|---|
| *A62B 18/08* | (2006.01) | |
| *A61M 16/00* | (2006.01) | |
| *A61M 16/06* | (2006.01) | |
| *A61M 16/08* | (2006.01) | |
| *G10L 15/22* | (2006.01) | |
| *H04R 1/02* | (2006.01) | |
| *H04R 1/08* | (2006.01) | |

(52) U.S. Cl.
CPC .......... *A62B 18/08* (2013.01); *A61M 16/021* (2017.08); *A61M 16/06* (2013.01); *A61M 16/0875* (2013.01); *G10L 15/22* (2013.01); *H04R 1/028* (2013.01); *A61M 2205/3375* (2013.01); *A61M 2205/3592* (2013.01); *A61M 2205/8206* (2013.01); *G10L 2015/223* (2013.01); *H04R 1/083* (2013.01); *H04R 2410/03* (2013.01); *H04R 2420/07* (2013.01)

(58) Field of Classification Search
CPC ... A62B 18/08; A61M 16/0875; A61M 16/06; H04R 1/08
See application file for complete search history.

(56) References Cited

U.S. PATENT DOCUMENTS

| | | | |
|---|---|---|---|
| 6,121,881 A | 9/2000 | Bieback et al. | |
| 6,619,288 B2 | 9/2003 | Demers et al. | |
| (Continued) | | | |

FOREIGN PATENT DOCUMENTS

| | | |
|---|---|---|
| CN | 105167252 A | 12/2015 |
| EP | 2673032 A1 | 12/2013 |
| (Continued) | | |

OTHER PUBLICATIONS

Written Opinion of the International Searching Authority and International Search Report for International Application No. PCT/US2017/038434, dated Aug. 29, 2017 (16 pp).

*Primary Examiner* — Peter S Vasat
*Assistant Examiner* — Cana A Gallegos
(74) *Attorney, Agent, or Firm* — DT Ward, PC; Donna T. Ward; Stuart S. Bray (57) ABSTRACT

The present disclosure presents a patient respiratory mask that is configured to pick up patient speech from within the patient respiratory mask utilizing a microphone and to transmit that speech to a speaker or other communications device and a method of patient communication utilizing the same.

8 Claims, 5 Drawing Sheets

(56) References Cited

U.S. PATENT DOCUMENTS

| | | |
|---|---|---|
| 7,269,266 B2 | 9/2007 | Anjanappa et al. |
| 7,342,502 B2 | 3/2008 | Harkins et al. |
| 7,532,934 B2 | 5/2009 | Lee et al. |
| 8,487,771 B2 | 7/2013 | Hsieh et al. |
| 8,616,205 B2 | 12/2013 | Tobias et al. |
| 8,818,522 B2 | 8/2014 | Mass et al. |
| 8,844,521 B2 | 9/2014 | McCarthy |
| 9,227,032 B2 | 1/2016 | Kwok et al. |
| 9,227,034 B2 | 1/2016 | Kapust et al. |
| 9,364,625 B2 | 6/2016 | Silver et al. |
| 9,498,658 B2 | 11/2016 | Kihlberg |
| 9,642,557 B2 | 5/2017 | Gavish et al. |
| 2005/0096096 A1* | 5/2005 | Birli .................. H04B 1/385 455/569.1 |
| 2005/0197172 A1 | 9/2005 | Davies |
| 2008/0216835 A1 | 9/2008 | McGinnis et al. |
| 2009/0205662 A1 | 8/2009 | Kwok et al. |
| 2015/0101600 A1* | 4/2015 | Miller ................. A61M 16/026 128/202.22 |
| 2015/0206408 A1 | 7/2015 | Lalonde et al. |
| 2015/0217143 A1* | 8/2015 | Palmer .................. A62B 18/08 128/202.27 |
| 2016/0001110 A1* | 1/2016 | Hamilton ............ G10L 21/0364 381/385 |
| 2016/0095997 A1 | 4/2016 | Kapust et al. |
| 2016/0101301 A1 | 4/2016 | Kihlberg |
| 2016/0199602 A1* | 7/2016 | Fernandez ............ A61M 16/01 128/202.13 |

FOREIGN PATENT DOCUMENTS

| | | |
|---|---|---|
| EP | 2776101 A1 | 9/2014 |
| WO | 00/69337 A1 | 11/2000 |
| WO | 2012/106775 A1 | 8/2012 |
| WO | 2013/067580 A1 | 5/2013 |

* cited by examiner

PATIENT RESPIRATORY MASK WITH INTEGRATED MICROPHONE AND METHOD OF PATIENT COMMUNICATION UTILIZING THE SAME

CROSS-REFERENCE TO RELATED APPLICATION

This patent application claims priority to U.S. Provisional Application No. 62/353,099 filed Jun. 22, 2016, which is incorporated herein by reference in its entirety.

BACKGROUND

The present disclosure relates patient respiratory masks, and in particular, patient respiratory masks, such as continuous positive air pressure (CPAP) or other (e.g., bi-level positive airway pressure (BiPAP)) devices, said respiratory masks that include a microphone, the microphone configured to interface with a wired or wireless speaker and/or a wired or wireless communications device, such as a telephone.

In a clinical setting, with a patient that requires the use of a respiratory mask that restricts the ability to communicate naturally, coherent conversation with visitors or via telephone is universally difficult. This is due, at least in part, to the intervening plastic material as well as to noise of the airflow and machinery.

Accordingly, there is a need in the art for a patient respiratory mask that is configured to pick up patient speech from within the patient respiratory mask or associated accessories, utilizing a microphone, and transmitting that speech to an external speaker or other communications device.

SUMMARY

The above-described and other problems and disadvantages of the prior art are overcome or alleviated by the present patient respiratory mask that includes a microphone, the microphone configured to interface with a wired or wireless speaker and/or a wired or wireless communications device, such as a telephone.

In exemplary embodiments, the microphone is a noise-cancelling microphone. In further embodiments, the microphone includes or is associated with at least one noise filter. In further exemplary embodiments, one or more of the microphone, speaker and communications device is in a wireless configuration.

In further exemplary embodiments, an on-board speaker is integrated into a portion of the respiratory mask coupler. In further exemplary embodiments, a speaker is external to the mask coupler.

In additional exemplary embodiments, the patient respiratory mask includes an internal and/or coupler adapted noise cancelling microphone with wireless, e.g., Bluetooth, capability. In further exemplary embodiments, the microphone signal is processed utilizing noise-cancelling sound processing. In exemplary embodiments, the microphone is attached to or built into a respiratory mask or mask fluid delivery tube.

In additional exemplary embodiments, the respiratory mask includes a coupler between a fluid delivery tube and a facial mask portion, the coupler including one or more of a microphone, speaker, wiring, processor, or communications device. In exemplary embodiments, one or more of the preceding elements are embedded in or provided through a portion of the coupler. In further exemplary embodiments, one or more of the elements described herein are embedded in or provided through a device connected to the coupler via power and/or signal wiring.

In further exemplary embodiments, the microphone is configured to wirelessly transmit a patient's voice, via Bluetooth technology, to a Bluetooth speaker in proximity to and in communication with the Bluetooth transmitter. In further exemplary embodiments, the microphone is configured to wirelessly transmit a patient's voice, via Bluetooth technology, to a Bluetooth-enabled smartphone in proximity to and in communication with the Bluetooth speaker and/or the Bluetooth transmitter. While a Bluetooth speaker and an exemplary Bluetooth smartphone are specifically described, the present disclosure contemplates other Bluetooth communications devices. And while Bluetooth is specifically described, the present disclosure contemplates other wireless technologies, including but not limited to Wi-Fi.

The above-discussed and other features and advantages of the present invention will be appreciated and understood by those skilled in the art from the following detailed description and drawings.

BRIEF DESCRIPTION OF THE DRAWINGS

Referring now to the drawings, wherein like elements are numbered alike in the following FIGURES.

DETAILED DESCRIPTION

As was noted above, the present disclosure relates to a patient respiratory mask that includes a microphone disposed thereon, the microphone is configured to interface with a wired or wireless speaker and/or a wired or wireless communications device, such as a telephone. While the following is described in reference to various exemplary embodiments, the present disclosure is not so limited.

In some exemplary embodiments, the microphone is a noise-cancelling microphone. In further embodiments, the microphone includes or is associated with at least one noise filter. In further exemplary embodiments, one or more of the microphone, speaker and communications device is wireless. It is to be understood that reference to a component, such as a microphone, speaker, etc., as being wireless or transmitting wirelessly encompasses configurations wherein such device is connected to a component that includes a wireless transmitter and/or receiver. Accordingly, any reference herein to a "wireless" component should be read to encompass such a construction.

In further exemplary embodiments, an on-board speaker is integrated into a portion of the respiratory mask. In further exemplary embodiments, a speaker is external to the mask.

As we have noted, in exemplary embodiments, the patient respiratory mask includes an internal and/or coupler- or tube-adapted noise-cancelling microphone with wireless, e.g., Bluetooth, capability. In exemplary embodiments, the microphone is attached to or built into a respiratory mask, a coupler designed to attach to the mask tube interface, or mask fluid delivery tube (e.g., for oxygen, air or some other gas). In additional exemplary embodiments, the coupler includes one or more of a microphone, a speaker, wiring, processor and a communications device. In exemplary embodiments one or more of the preceding elements are embedded in or provided through a portion of the coupler.

As we have also noted, further exemplary embodiments, the microphone wirelessly transmits a patient's voice, via Bluetooth technology, to a Bluetooth speaker in proximity to and in communication with the Bluetooth transmitter. Reference herein to a "Bluetooth" device refers to a device that is enabled to use Bluetooth technology.

In further exemplary embodiments, the microphone wirelessly transmits a patient's voice, via Bluetooth technology, to a Bluetooth smartphone in proximity to and in communication with the Bluetooth speaker and/or Bluetooth transmitter. While a Bluetooth speaker and an exemplary Bluetooth smartphone are specifically described, the present disclosure contemplates other Bluetooth communications devices.

Figure 1:
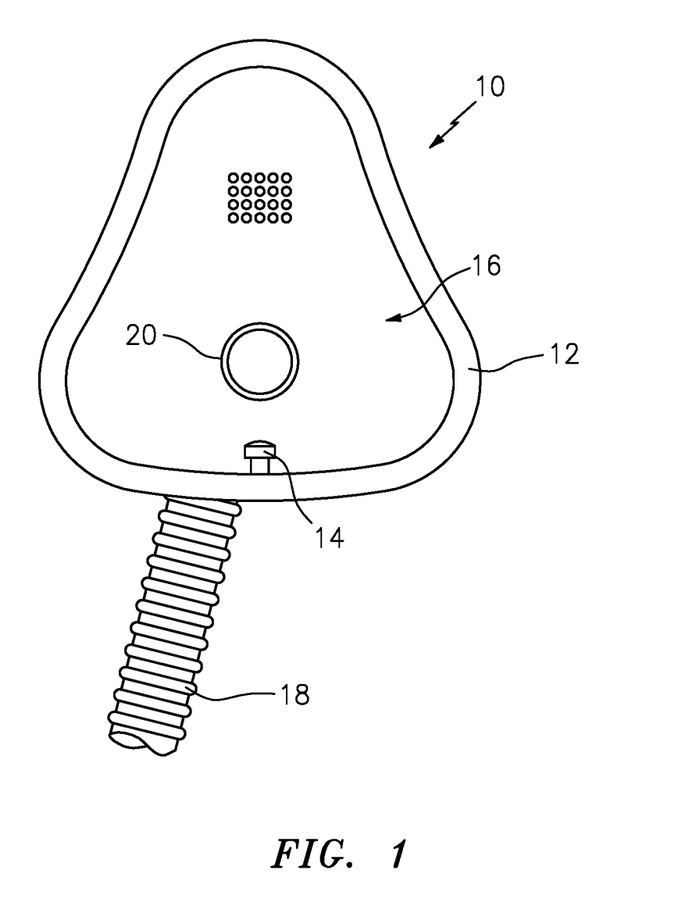
FIG. 1 is a rear elevation view of an exemplary respiratory mask including a microphone in accordance with exemplary embodiments of the present disclosure.

Referring now to FIG. 1, one exemplary patient respiratory mask in accordance with the present disclosure includes an exemplary microphone provided therein. In exemplary embodiments, the respiratory mask is a CPAP (or BIPAP) respiratory mask, shown generally at 10, with a mask portion 12 and a Bluetooth microphone 14 that is incorporated within a fluid airspace, shown generally at 16, of the mask 10 near the mouth (not shown) of a patient. The exemplary mask also includes a fluid delivery tube 18 and at least one mask inlet 20.

In exemplary embodiments, the microphone 14 is mounted on or is provided within the material of the mask. In another exemplary embodiment, the microphone is provided in a separate microphone tube (not shown) that may extend at least partially into the fluid airspace of the mask 10. In further exemplary embodiments, the microphone tube is at least partially sealed, for example via plastic or a membrane that is at least moderately transparent to sound but that also separately maintains the integrity of the fluid airspace 16 within the respiratory mask 10. Such an exemplary microphone tube may be provided within or be mounted to the respiratory mask 10, a fluid delivery tube 18, or any coupler 22 or portions intermediate the fluid delivery tube 18 the respiratory mask 10.

Figure 2:
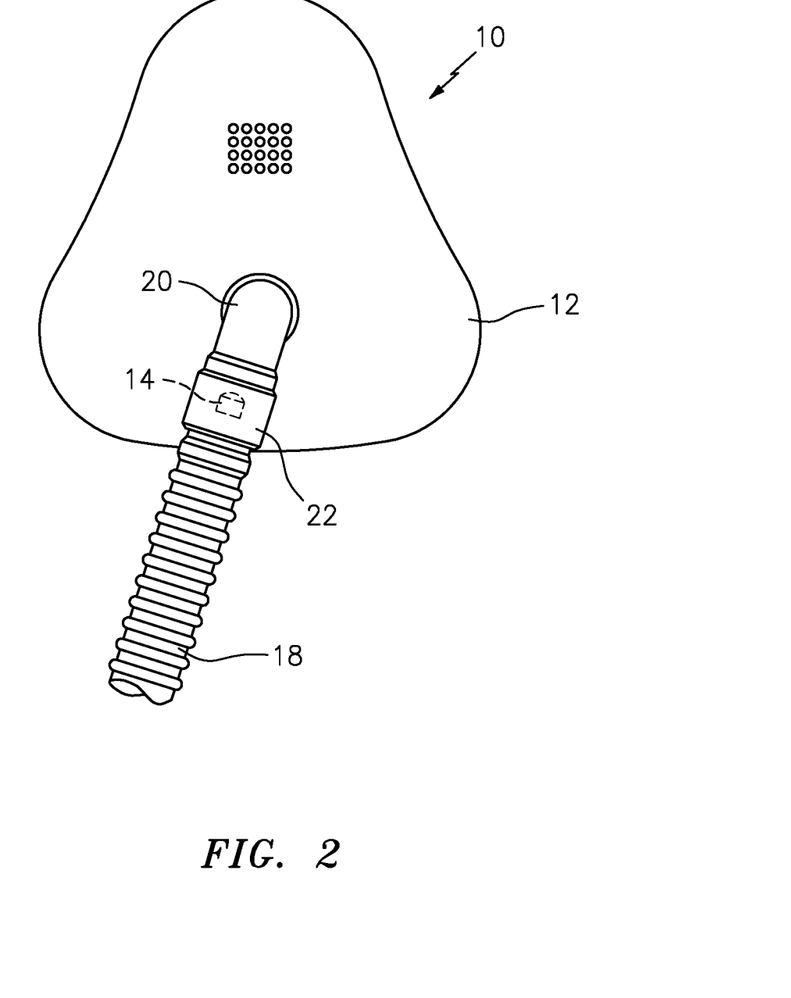
FIG. 2 is a perspective view of an exemplary respiratory mask utilizing a microphone coupler provided on the fluid delivery tube near the respiratory mask in accordance with exemplary embodiments of the present disclosure.

Referring now to FIG. 2, another exemplary patient respiratory mask 10 incorporates such Bluetooth microphone 14 into a coupler device 22 that is positioned between the fluid delivery tube 18 and the respiratory mask 10. In exemplary embodiments, the coupler 22 is sized and configured to provide a friction fit for the mask inlet 20 on one side and for the fluid delivery tube 18 on the other side.

Figure 3:
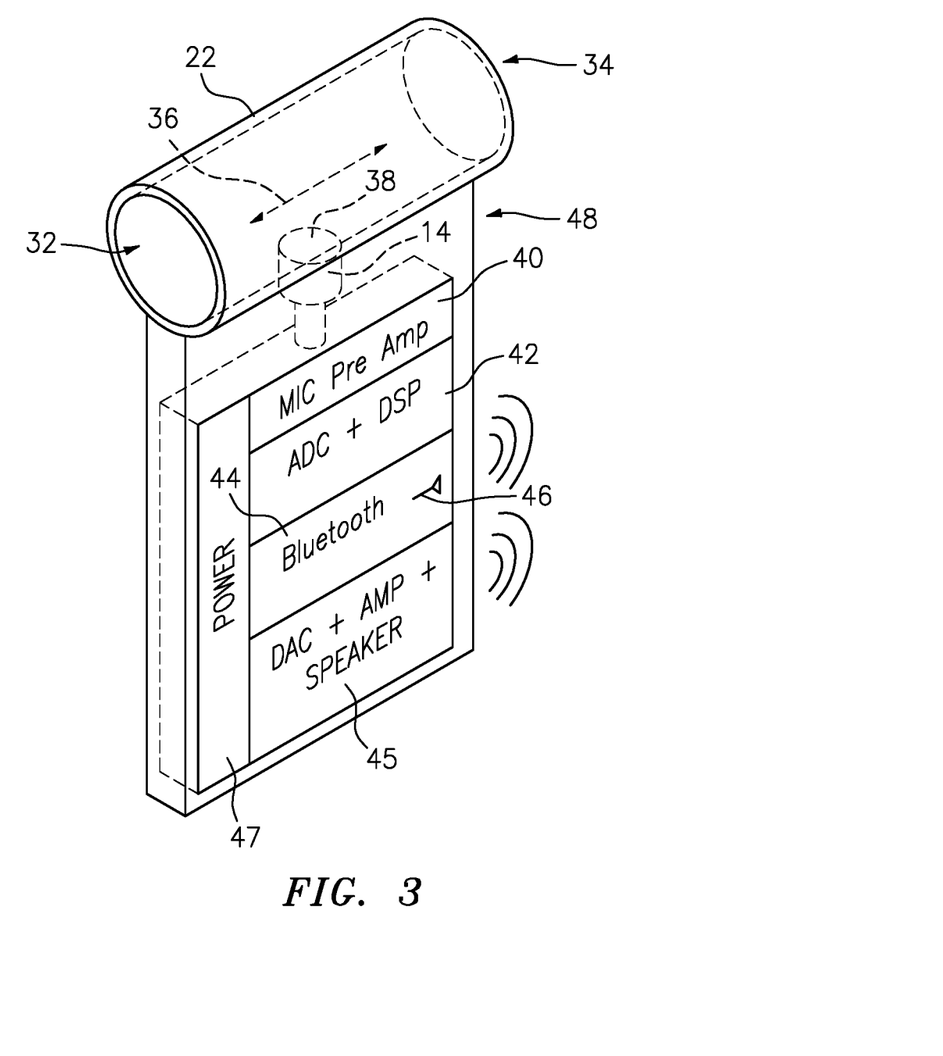
FIG. 3 is a perspective view of an exemplary coupler device incorporating a microphone, including a schematic of communications components for the coupler in accordance with exemplary embodiments of the present disclosure.

Referring to FIG. 3, an exemplary coupler 22 includes a mask inlet side, shown generally at 32, a fluid supply tube side, shown generally at 34, with bulk air flow traversing the interior of the tube generally at the arrows of 36.

In an exemplary embodiment, a microphone 14 is separated from the bulk air flow 36 by a filter 38, which may be configured to filter one or more sound characteristics or to simply shield the microphone from bulk air flow. The filter 38 may be a membrane, acoustic mesh, or any other convenient sound transmitting material.

In the illustrated exemplary embodiment, the microphone is illustrated as being operatively connected to a microphone pre-amplifier 40, an equalization component 42 (for example an analog to digital converter (ADC) and digital signal processor (DSP)), a Bluetooth transmitter 44, a sound output component, such as a digital to analog converter (DAC), amplifier (Amp) and speaker 45, an antenna 46 and a power supply 47, such as a battery or wired power adapter. These components are illustrated in this exemplary embodiment as being both connected to the microphone and as being housed on a protruding portion 48 of the coupler 22. However, it should be recognized that the microphone may be configured on-board the coupler 22 with more or fewer associated components, with some components or processes omitted or performed elsewhere, e.g., on the exterior of the coupler 22, remote from the coupler 22, etc. Additionally, the coupler can take any convenient shape when housing such components, as long as connecting portions 32 and 34 are configured to connect to the mask inlet 20 and the fluid delivery tube 18, respectively.

Figure 4A:
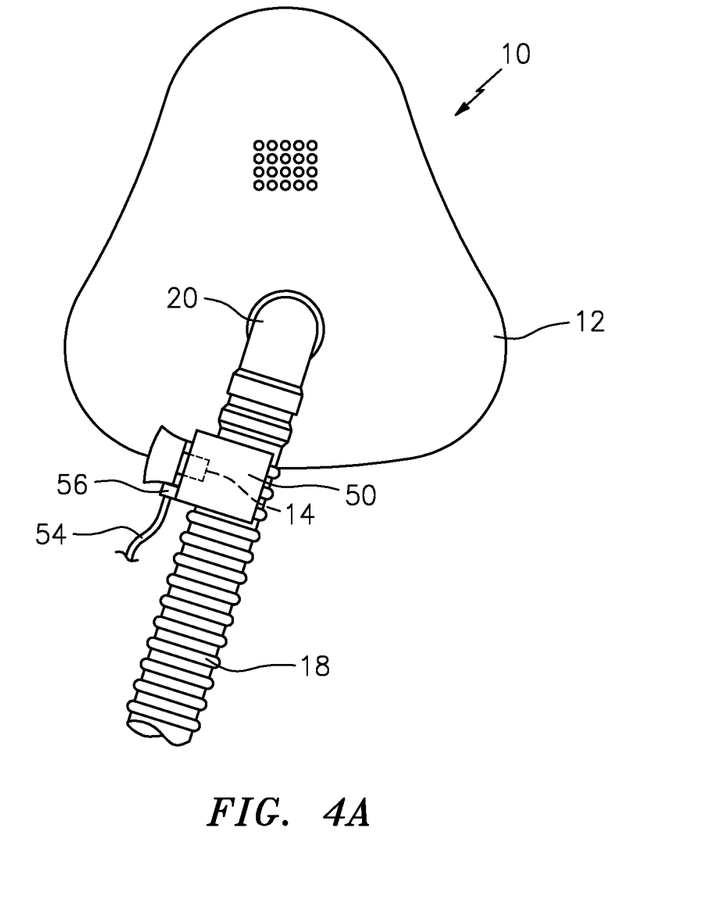
FIG. 4A is a perspective view of an exemplary clip-on accessory including a microphone in accordance with the exemplary embodiments of the present disclosure.

In exemplary embodiments, the coupler may be configured to attach to the fluid delivery tube, regardless of any variation in tube diameter (e.g., differences in configurations warranting use of a 19 mm standard tube vs. a 15 mm thin tube). Thus, exemplary embodiments provide a universal attachment (e.g., as a clip on, etc., as shown in FIG. 4) configured to fit a wide array of tubes and breathing apparatuses.

Figure 4B:
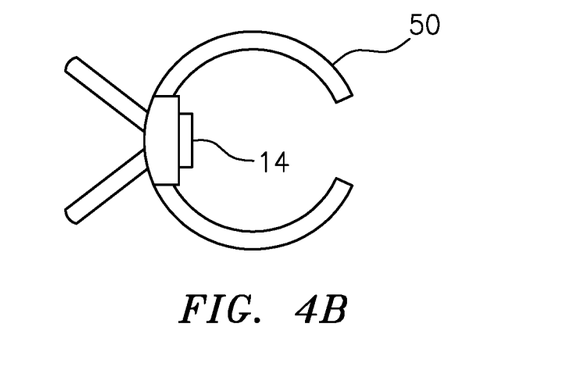
FIG. 4B is a side elevation view of an exemplary clip-on accessory including a microphone in accordance with the exemplary embodiments of the present disclosure.

In other exemplary embodiments, the microphone or other electronic components are configured to attach externally (for example as a clip-type attachment, among others) to the respiratory mask 10 but in close proximity to the patient's fluid airspace (see 16 in FIG. 1). Referring now to FIG. 4A, a clip 50 is illustrated with a microphone unit 14 provided on an underside of the clip. In exemplary embodiments, the clip 50 also interfaces with a power and signal wire 54 via a port 56. While such a clip may be configured to attach anywhere that is convenient to place the microphone unit 14 near a sound transmitting surface, for example the inlet portion 20 of mask 10 or an exterior portion of a coupler 22, FIG. 4 illustrates provision of the clip 50 over a portion of the fluid deliver hose 18, with the microphone unit against or proximate the material of the hose to pick up sound vibrations transmitted through the hose. It should be recognized that while FIG. 4 illustrates a wired configuration, the microphone unit can also be configured with a battery and a wireless (e.g., Bluetooth) transmitter. FIG. 4B illustrates an exemplary side elevation view of the clip 50, with microphone 14 positioned to be near tube 18 in an installed position.

Figure 5:
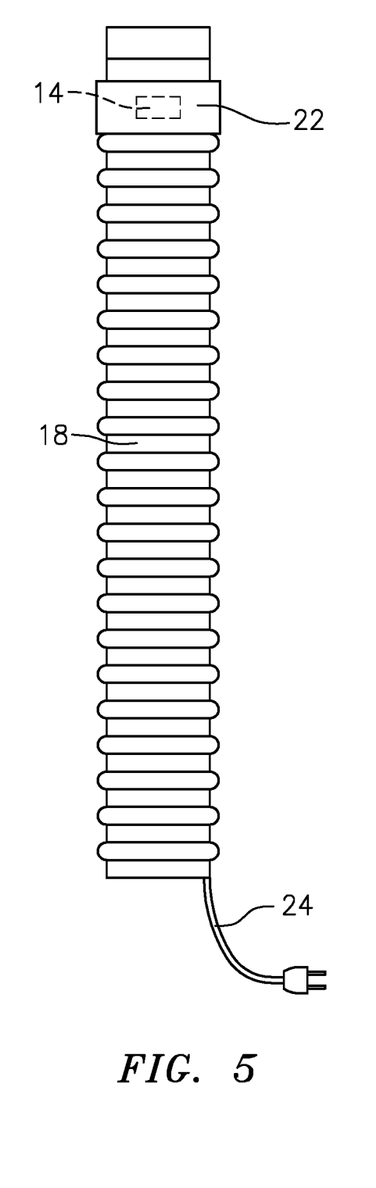
FIG. 5 is a front elevation view of an exemplary wired tube and respiratory mask coupler including a microphone in accordance with exemplary embodiments of the present disclosure.

Referring now to FIG. 5, an exemplary fluid delivery tube 18 is illustrated as including an integrated coupler 22 that incorporates an exemplary microphone 14 (see FIG. 2) therein and is attachable to or integral to respiratory fluid delivery tube 18. An exemplary power cord 24 runs at least along a portion of the tube 18 to the microphone 14 (which may be configured in a wired or wireless, e.g., Bluetooth, arrangement). As we have noted above, the coupler may also include other components, such as processing or filtering components, a wireless transmitter, etc., in addition to or alternative to the microphone, such as a speaker, wiring or any other type of communications device.

In further exemplary embodiments, the microphone 14 may be configured as a wired microphone utilizing the exemplary cord 24 or another cord for data transmission. In additional exemplary embodiments, the microphone may be wireless and may be connected to a battery source, with no cords running along a portion of the tube 18.

In further exemplary embodiments, an exemplary cord can be configured with one or more clips to secure it to the hose 18 or as an integral part of the hose 18, for example embedded or permanently attached to the tube 18 or to a tube wiring harness. Exemplary wire harness clips 62 are illustrated as attaching a cord 24 to tube 18 in FIG. 6. In exemplary embodiments, the cord 24 is configured as a wiring harness secured at one or more places via harness clips 62, with the cord connectable to a coupler 22 (as in FIGS. 2 and 3) or a mask (as in FIG. 1).

Figure 6:
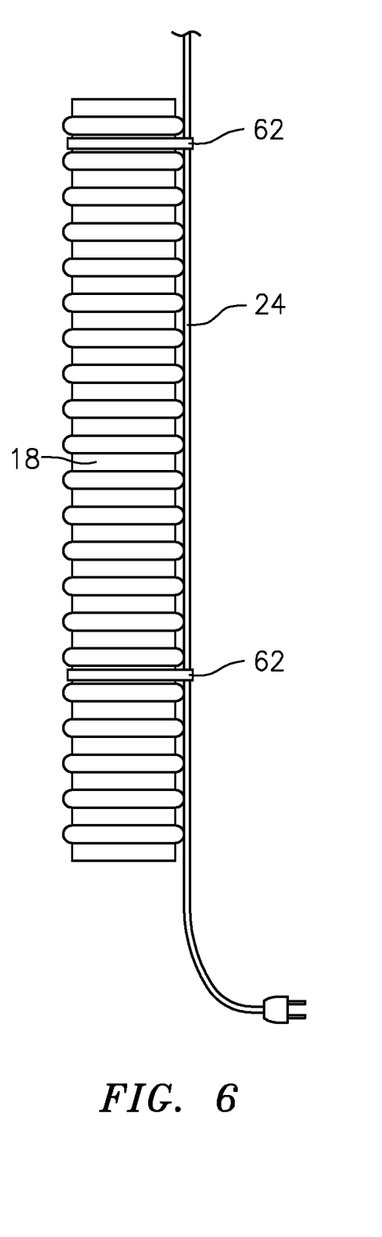
FIG. 6 is a side elevation view of exemplary tube and cord lengths secured to one another via multiple harness clips in accordance with exemplary embodiments of the present disclosure.

For any wired configurations, the remote (from the mask) end of the cord 24 may be configured to connect to additional components, such as a speaker, processor, network, power, etc.

Exemplary embodiments contemplate non-rechargeable, battery-driven Bluetooth microphones as well as rechargeable battery Bluetooth microphones with a port or cable or wireless connection for recharging via an external power source, or directly corded microphones (providing constant power).

In exemplary embodiments, the patient respiratory mask, inclusive of the Bluetooth microphone, is configured as a disposable device. In exemplary embodiments, one or more components, such as the mask, coupler or hose, is configured as a disposable product to have a pre-determined working lifetime. In further exemplary embodiments, life indicators may be used to identify an end of the working respirator mask lifetime determined from unpacking from a sterile field. In a further exemplary embodiment, a battery in communication with the microphone is configured to expire or switch off at end of the working respirator mask lifetime. In additional exemplary embodiments wherein one or more components is provided in the above-described coupler, such coupler may also, or in the alternative, include one or more life indicators.

In other exemplary embodiments, the patient respiratory mask and/or fluid delivery tube is configured to be reusable, with the Bluetooth microphone being at least partially water resistant. In further exemplary embodiments, the Bluetooth microphone is waterproof or is housed in a waterproof enclosure. In such exemplary embodiments, the patient respiratory mask and/or tube may be configured with a Bluetooth microphone configured to withstand cleaning via use of cleaning agents, e.g., enzymatic cleaning solutions, rinses, disinfectants and pasteurizations, among others. Further exemplary embodiments provide a Bluetooth microphone or microphone enclosure configured to withstand the effects of cleaning as well as effects of drying at utility or other stations.

Exemplary embodiments of the present disclosure also relate to an exemplary system with a patient respiratory mask positioned on a patient, the respiratory mask including a Bluetooth noise cancelling microphone within or adjacent to the patient's fluid airspace, and at least one external Bluetooth communications device. In the illustrated exemplary embodiment, a Bluetooth speaker and a Bluetooth smartphone are illustrated as being in communication with the microphone. In exemplary embodiments, at least the microphone and one external Bluetooth communication device are pre-paired to permit instantaneous connection when within the proper proximity. In other exemplary embodiments, the Bluetooth microphone continually broadcasts pairing information and is open for pairing subject to confirmation by the external Bluetooth communications device. Other exemplary communications devices are also contemplated herein, including, without limitation, personal assistants, including media platforms such as the Google Home or Amazon Echo/Tap/Alexa, etc., that also might have a speaker that is usable for patient communications as well as the ability to accept commands for any of its functions (e.g., to play music or call someone via voice over Internet protocol or other means). Other exemplary embodiments have a speaker integral with the mask, coupler or fluid tube. Additionally, other communications protocols may be used in conjunction with the above-described wireless protocols and others (e.g., non-Bluetooth wireless protocols), such as Wi-Fi.

As we have noted, a speaker or other communications device may be external or may be integrated into the mask portion, coupler or fluid delivery tube. Additionally, such speaker or other communications device can be configured to communicate wirelessly or in a wired mode. In a further exemplary aspect, both modes are configured, and the system is configured to automatically or manually (via a switch or application) switch modes.

In further exemplary embodiments an application running on a processor controls one or more aspects of the system, including without limitation: speaker or communications device mode; noise filtering/canceling or processing parameters; microphone parameters; wireless connections to devices; and monitoring for new devices in range.

In further exemplary embodiments, power for one or more components is supplied by a power cable with any convenient terminal ends, for example 110 volt outlet termination, USB, lightning connector, etc.

In other exemplary embodiments, bone induction or an in-ear, behind the ear or in-canal hearing aid provides or delivers a sound signal to the patient, with bone induction or hearing aid equipment wired to or wirelessly communicating with the respiratory mask system.

In exemplary embodiments, when the user (patient) of the respiratory mask speaks, their voice will be captured by the noise canceling microphone as the sound hits the interior structure of the mask and/or travels down the tube. Once the voice is captured in the device, it is transferred via Bluetooth technology to a free-standing speaker where their voice will be amplified. In other exemplary embodiments, the voice is transferred to a speaker on the mask, coupler or tube where the voice will be amplified.

In other exemplary embodiments, the system is configured to distinguish between direct human interaction (conversation) and digital interaction (e.g., voice signals from a mobile phone) and automatically switch output to one of plural possible wireless communications devices depending on the detected signal. Alternative automatic or manual switching is further contemplated herein with regard to exemplary embodiments, for switching between a nearby Bluetooth speaker and a communications device (e.g., a mobile telephone, facilitating patient conversation with a remote individual). In other embodiments, multiple Bluetooth devices may be connected at the same time via bridging capabilities. Such a switching or bridging capability may be e.g., provided alongside the microphone or anywhere in range of the Bluetooth microphone. In other embodiments, multiple Bluetooth devices may be connected at the same time via multiple connections or modes.

It will be apparent to those skilled in the art that, while exemplary embodiments have been shown and described, various modifications and variations can be made to the invention disclosed herein without departing from the spirit or scope of the invention. Also, the exemplary implementations described above should be read in a non-limiting fashion, both with regard to construction and methodology. Accordingly, it is to be understood that the various embodiments have been described by way of illustration and not limitation.

What is claimed is:

1. A device for communications with a respiratory mask user, the device comprising:
    a microphone, the microphone configured to pick up speech from the respiratory mask user;
    a coupler, the coupler configured to couple the microphone with a respiratory mask, the respiratory mask comprising:
        a mask portion, wherein the mask portion comprises a mask inlet; and a fluid delivery tube;
    wherein the coupler comprises a tube, wherein the tube defines an interior fluid airspace configured for traversal of bulk air flow between the mask portion and the fluid supply tube, the coupler tube comprising:
        a fluid supply tube side, the fluid supply tube side configured for direct attachment to the fluid supply tube; and
        a mask inlet side, the mask inlet side configured for attachment to the mask inlet; and
    a housing, the housing comprising:
        the microphone, wherein the microphone is positioned in close proximity to the interior fluid airspace of the coupler tube, and wherein the microphone is isolated from fluid communication with the interior fluid airspace of the coupler tube; a power supply or a port to connect to a power supply; and
        a speaker.

2. The device of claim 1, wherein the housing comprises a processor, a communications device, and/or a port.

3. The device of claim 2, wherein the communications device comprises a wireless transmitter.

4. The device of claim 1, wherein the housing comprises a preamplifier and/or an amplifier.

5. The device of claim 1, wherein the power supply comprises a battery or a wired power adapter.

6. The device of claim 1, wherein the microphone is separated from the interior of the tube by a filter.

7. The device of claim 6, wherein the filter comprises a sound transmitting material.

8. The device of claim 1, wherein the microphone comprises a noise-cancelling microphone.

* * * * *